United States Patent
Hayasawa et al.

(10) Patent No.: US 6,908,633 B2
(45) Date of Patent: Jun. 21, 2005

(54) PROTEIN HYDROLYZATES, PROCESS FOR PRODUCING THE SAME AND DRINKS AND FOODS CONTAINING THE PROTEIN HYDROLYZATES

(75) Inventors: Hirotoshi Hayasawa, Zama (JP); Yoshitaka Tamura, Zama (JP); Hiroshi Miyakawa, Zama (JP); Toshikazu Shichino, Zama (JP); Yasushi Kawaguchi, Zama (JP); Hirokatsu Kanehara, Zama (JP)

(73) Assignee: Morinaga Milk Industry Co., Ltd., Tokyo (JP)

( * ) Notice: Subject to any disclaimer, the term of this patent is extended or adjusted under 35 U.S.C. 154(b) by 310 days.

(21) Appl. No.: 10/148,274

(22) PCT Filed: Mar. 12, 2001

(86) PCT No.: PCT/JP01/01902

§ 371 (c)(1),
(2), (4) Date: May 29, 2002

(87) PCT Pub. No.: WO01/68672

PCT Pub. Date: Sep. 20, 2001

(65) Prior Publication Data

US 2003/0072863 A1 Apr. 17, 2003

(30) Foreign Application Priority Data

Mar. 13, 2000 (JP) ........................................ 2000-069023
May 16, 2000 (JP) ........................................ 2000-142886

(51) Int. Cl.⁷ .............................. A23C 9/12; A23J 1/00
(52) U.S. Cl. .............................. 426/34; 426/42; 426/55; 426/56; 426/580; 426/656; 426/657
(58) Field of Search .............................. 426/34, 42, 55, 426/56, 580, 656, 657, 478

(56) References Cited

U.S. PATENT DOCUMENTS 4,670,268 A 6/1987 Mahmoud 4,981,704 A 1/1991 Thibault

FOREIGN PATENT DOCUMENTS

| JP | 62-191041 A | 8/1987 |
| JP | 3-240436 | 10/1991 |
| JP | 403240436 | * 10/1991 |
| JP | 4-190797 A | 7/1992 |
| JP | 05-276896 | 10/1993 |
| JP | 7-264993 A | 10/1995 |
| JP | 10-17596 A | 1/1998 |
| WO | WO 97/01966 | 1/1997 |

OTHER PUBLICATIONS

Mahmoud et al, "Enzymatic Hydrolysis of Casein: Effect of Degree of Hydrolysis on Antigenicity and Physical Properties", Journal of Food Science, 57 (1992) Sep./Oct., No. 5, Chicago, IL US; XP 000311013.

Lee, "Food–processing approaches to altering allergenic potential of milk–based formula", Journal of Pediatrics, Nov. 1992, Mosby–Year Book, St. Louis, MO, vol. 121, Nr. 5, Part 2, pp. S47–S50; XP002102943; ISSN 0022–3476.

* cited by examiner

Primary Examiner—Leslie Wong
(74) Attorney, Agent, or Firm—Nixon & Vanderhye P.C.

(57) ABSTRACT

A protein hydrolysate comprising at least two types of peptides, characterized in that the rate of hydrolysis of protein is from 30 to 45%, the number average molecular weight is 300 or less, and the ratio of a weight average molecular weight to the number average molecular weight is greater than 1 and 2 or less, has excellent emulsifiability, and antigenicity thereof is low enough to be used for people who has predisposition to allergic diseases. This protein hydrolysate is obtained by hydrolysis of a protein starting material to a rate of hydrolysis in the range of 30 to 45%, and then bringing it into contact simultaneously or separately with two types of porous synthetic adsorbent respectively having an average pore radius of 2 to 8 nm and an average pore radius of 20 to 30 nm, the total surface area of the two porous synthetic adsorbents being in a range of 300 to 3000 m² per 1 g (protein equivalent) of the obtained protein hydrolysate, and recovering the non-adsorbed component.

2 Claims, No Drawings

PROTEIN HYDROLYZATES, PROCESS FOR PRODUCING THE SAME AND DRINKS AND FOODS CONTAINING THE PROTEIN HYDROLYZATES

This application is a 371 of PCT/JP01/01902 filed Mar. 12, 2001.

FIELD OF THE INVENTION

The present invention relates to protein hydrolysate, a manufacturing method therefor, and foods and drinks which contain the protein hydrolysate. In particular, the present invention relates to protein hydrolysate which has low antigenicity, and good emulsifiability, and to foods and drinks which contain this protein hydrolysate. In addition, the present invention relates to a manufacturing method for obtaining this protein hydrolysate at a high recovery rate.

DESCRIPTION OF THE RELATED ART

In recent years, there has been a trend toward increasing occurrences of food allergies and the importance of effective prevention and treatment of allergic incidence has increased.

With regard to incidence of food allergies, when infants ingest modified milk, modified powdered milk, or the like, the protein contained is sometimes absorbed into the body as it is in a state in which it is not sufficiently digested and still has antigenicity, and this is indicated as one of the causes for the incidence of diseases. For this reason, in order to prevent the incidence of allergic diseases in individuals who are believed to have a predisposition to allergic diseases, it is necessary for the modified milk and modified powdered milk ingested during infancy to have low antigenicity.

For this reason, conventionally, many protein hydrolysates which have a remaining antigenic activity of $10^{-6}$ or less have been developed by hydrolyzing a protein such as milk protein which is the antigenic substance, and reducing the antigenicity (for example, refer to Japanese Examined Patent Application, Second Publication No. Sho 54-36235; Japanese Examined Patent Application, Second Publication No. 62-61039; Japanese Examined Patent Application, Second Publication No. Hei 7-73507; Japanese Patent No. 2959747; and Japanese Unexamined Patent Application, First Publication No. Hei 8-228692). However, with regard to these protein hydrolysates, results for measurement of remaining antigenic activity using the sandwich ELISA method, which is a high sensitivity measurement method for remaining antigenic activity, show that the remaining antigenic activity is $10^{-7}$ or greater, and that some antigenicity remains (discussed below).

On the other hand, since the emulsifiability of proteins is reduced by a high degree of hydrolysis, there are the problems that in modified milk obtained using a highly hydrolyzed substance, the emulsified state of the fat globules in the milk cannot be maintained, and the fat globules aggregate and separate out. Thus, not only does modified milk in which the fat has separated out have a bad flavor and appearance, the absorption efficiency of the fat is low.

In order to overcome this problem, a protein hydrolysate which is superior in emulsifiability, which has a lower remaining antigenic activity, and which is obtained by hydrolysis of whey protein using three specific enzymes under specific pH conditions has been disclosed (Japanese Unexamined Patent Application, First Publication No. Hei 7-203844). However, the remaining antigenic activity of this hydrolysate is $10^{-5}$, and therefore the antigenicity is not sufficiently reduced (discussed below).

In these day in which the prevention and treatment of incidence of allergy has become a serious problem, reducing the remaining antigenic activity to as close as possible to zero will reduce the risk of the occurrence of food allergies and will provide safe foods and drinks. In addition, it is extremely important as a social responsibility of food makers.

SUMMARY OF THE INVENTION

Objects of the present invention are to obtain a protein hydrolysate having improved emulsifiability and further reduced antigenicity, specifically, a remaining antigenic activity of the protein reduced to the detection limit of the sandwich ELISA method, and/or to improve the recovery rate of the protein hydrolysate with respect to the protein starting material.

The inventors of the present invention completed the present invention by repeated research on various methods of manufacturing protein hydrolysate, in particular, the hydrolysis conditions for various protein starting materials and combinations of porous synthetic adsorbents, and the characteristics of the obtained protein hydrolysates.

The protein hydrolysate of the present invention is a protein hydrolysate comprising at least two types of peptides, in which the rate of hydrolysis of the protein is from 30 to 45%, the number average molecular weight is 300 or less, and the ratio of the weight average molecular weight to the number average molecular weight is greater than 1 and 2 or less. This protein hydrolysate has reduced antigenicity and superior emulsifiability when compared with conventional protein hydrolysates.

The method of manufacturing the protein hydrolysate of the present invention comprises carrying out hydrolysis of a protein starting material to a rate of hydrolysis within the range of 30 to 45%, and bringing the obtained protein hydrolysate into contact simultaneously or separately with two types of porous synthetic adsorbent respectively having an average pore radius in the range of 2 to 8 nm and an average pore radius in the range of 20 to 30 nm, the total surface area of the two porous synthetic adsorbents being in a range of 300 to 3000 $m^2$ per 1 g (protein equivalent) of the obtained protein hydrolysate, and recovering the non-adsorbed component. Compared with conventional methods of manufacturing protein hydrolysate, the method of manufacturing the protein hydrolysate of the present invention is superior in its recovery rate of protein hydrolysate with respect to the protein starting material, and in the reduced antigenicity and improved emulsifiability of the obtained protein hydrolysate.

In addition, in this method of manufacturing, it is preferable for the porous synthetic adsorbents to be used such that the ratio of the surface area of the porous synthetic adsorbent having an average pore radius of 2 to 8 nm to the porous synthetic adsorbent having an average pore radius of 20 to 30 nm is in a range of 4:6 to 6:4.

The food and drink products of the present invention comprise the above-mentioned protein hydrolysate of the present invention. The food and drink products of the present invention can be made as food and drink products for the prevention of allergies, or as foods and drinks for allergy patients, and in particular, they can be made as modified milk or modified milk powders obtained from protein derived from milk as the starting material protein.

Consequently, additional embodiments of the present invention use the above-mentioned protein hydrolysate in foods and drinks for the prevention of allergies, and foods and drinks for allergy patients, and in the manufacture thereof.

BEST MODE FOR CARRYING OUT THE INVENTION

In the present specification, with the exception of the rate of hydrolysis, percentages indicate percentage by weight unless otherwise indicated. In addition, in the present specification, protein equivalent is the value of the amount of nitrogen multiplied by 6.38.

The protein hydrolysate of the present invention is a protein hydrolysate which contains at least two types of peptide, and the isolation and refinement of single peptides from protein hydrolysate does not fall within the scope of the present invention.

1) Number Average Molecular Weight and Weight Average Molecular Weight

In general, number average molecular weight and weight average molecular weight express the average value of the molecular weight of a macromolecular compound based on differing indicators as explained below, and as described in reference documents (The Society of Polymer Science, Japan, "Basic High Polymer Science", pages 116 to 119, Tokyo Kagaku Doujin KK, 1978).

In more detail, macromolecular compounds such as protein hydrolysates are heterogeneous substances. Moreover, since there is a distribution in their molecular weight, in order for management in a physico-chemical manner, it is necessary to indicate the molecular weight of a protein hydrolysate at an average molecular weight. The number average molecular weight (hereinafter referred to as Mn) is the average for the number of molecules. If the molecular weight of a peptide chain i is Mi, and the number of molecules is Ni, Mn can be defined by the following formula:

$$Mn = \sum_{i=1}^{\infty} Mi\, Ni \Big/ \sum_{i=1}^{\infty} Ni$$

In addition, the weight average molecular weight (hereinafter referred to as Mw) is the average for the weight, and is defined by means of the following formula:

$$Mw = \sum_{i=1}^{\infty} Mi^2\, Ni \Big/ \sum_{i=1}^{\infty} Mi\, Ni$$

As is clear from the above formulae, the relationship between Mn and Mw is always such that Mn≦Mw. Mn is susceptible to contributions from low molecular weight substances contained in macromolecular compounds. In contrast, Mw is easily influenced by high molecular weight substances.

Conventionally, for unhydrolyzed protein molecules having a single determined amino acid sequence, there is no distribution in the molecular weight, and Mn=Mw. When the molecule has been hydrolyzed, since the molecular weights of the various fragments of peptide generated vary greatly, the molecular weight distribution has a broad range. In more detail, the greater the width of this distribution, the greater the difference between Mn and Mw. Consequently, the value of the ratio of the weight average molecular weight to the number average molecular weight, in other words, the value of Mw/Mn, is used as an indicator of the breadth of the molecular weight distribution of a protein hydrolysate.

In the present invention, the number average molecular weight and the weight average molecular weight use values measured using high performance liquid chromatography and a GPC analysis system which are known to those skilled in the art (for example, Nobuo Ui et al, "High Performance Liquid Chromatography of Proteins/Peptides", Chemical Zoukan No. 102, page 241, Kagaku Doujin KK, 1984).

In the protein hydrolysate of the present invention, the number average molecular weight is 300 or less, and is preferably 200 or more and 300 or less. In addition, the ratio of the weight average molecular weight to the number average molecular weight is greater than 1 and 2 or less.

2) Rate of Hydrolysis of Protein

In the present invention, the rate of hydrolysis of protein represents the weight ratio of formol nitrogen to the total amount of nitrogen within the protein hydrolysate. The total amount of nitrogen can be measured using the Kjeldahl method which is known by those skilled in the art. In more detail, as described in "Food Analysis Methods", edited by the Japanese Society for food Science and Technology, page 102, Kourin KK, 1984, and elsewhere, mercury, mercuric (II) oxide, or copper sulfate is added as a hydrolysis promoting agent to a sample, and thermolysis is carried out in concentrated sulfuric acid, potassium sulfate or sulfuric acid, or fuming sulfuric acid to convert the nitrogen within the sample to ammonium sulfate. To this, a strong alkali is added, steam distillation is carried out, the free ammonium is scavenged by a prescribed amount of acid, and then back titration with an excess of acid is carried out to calculate the amount of scavenged ammonia. From this amount, the total amount of nitrogen can be calculated. The formol nitrogen is the determined quantity of amino acid calculated by means of formol titration of a method known to those skilled in the art for titration of free amino acid by a standard alkali solution. For example, as described in Mitsuda et al, "Food Engineering Experiments", First Volume, page 547, Yokendo, 1970, a sample is neutralized (or adjusted to a pH of 7) in advance by 0.1 N sodium hydroxide or 0.1 N hydrochloric acid, and formalin added. As a result, an oxymethyl derivative is formed as in:

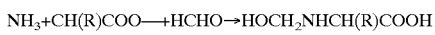

NH$_3$+CH(R)COO—+HCHO→HOCH$_2$NHCH(R)COOH

Therefore, this is titrated using phenolphthalein or using a 0.1 N sodium hydroxide standard solution using a potentiometer. The amount of nitrogen calculated as [0.1N of 1 ml NaOH]=[1.4 mg α-amino acid nitrogen] is the amount of formol nitrogen.

From the values of total nitrogen and formol nitrogen obtained in the above-described ways, the rate of hydrolysis can be calculated by:

rate of hydrolysis (%)=(formol nitrogen/total nitrogen)×100

In the present invention, the rate of hydrolysis of protein is 30 to 45%.

In the following, the present invention will be explained in more detail. However, in order for easy understanding of the present invention, the method of manufacturing (hereinafter referred to as the method of the present invention) the protein hydrolysate of the present invention will be explained first.

The protein starting material used in the method of the present invention is animal protein derived from animal milk, eggs, fish flesh, meat, and the like, plant protein derived from soy beans, wheat, and the like, microbial protein derived from fungi, yeast, bacteria, and the like, or arbitrary mixtures thereof, and is not particularly limited. In addition, protein concentrate obtained by concentration of these proteins by means of processes such as ultrafiltration, ion exchange resin, and the like can also be used. In addition, hydrolyzed product obtained by slight hydrolysis of the above-mentioned protein in advance, and protein hydrolysate having a comparatively large molecular weight can also be used as the starting material.

This protein starting material is dispersed in water or hot water and dissolved. The concentration of the resulting solution is not particularly limited, but it is preferable from the point of efficiency and processability that the protein concentration normally be approximately 5 to 15%.

Next, it is preferable from the point of view of the prevention of spoiling due to contamination by bacteria for this protein solution to be heat sterilized at 65 to 90° C. for from 1 to 30 minutes.

The means for hydrolysis of the protein starting material of the present invention is not particularly limited as long as it is possible for adjustment to a rate of hydrolysis of 30 to 45% of the protein, and can be carried out using a protease method according to normal methods. More specifically, the hydrolysis conditions according to the protease method, such as the type of enzyme, the amount, temperature, pH, time period for the hydrolysis, and the like, with which it is possible to adjust the rate of hydrolysis of the protein to 30 to 45%, are established by preliminary testing, and thereafter the protein hydrolysate can be prepared.

Moreover, the rate of hydrolysis is used as an indicator of the degree of hydrolysis, and as will also be clear from the Tests explained below, the reason why the range thereof is made to be from 30 to 45% is that when the rate of hydrolysis is less than 30%, antigenicity remains, and when hydrolysis proceeds to a rate of hydrolysis exceeding 45%, the emulsifiability of the protein hydrolysate which is the final product is degraded.

Examples of the protease used in the hydrolysis method of the protein starting material of the present invention are endoproteases or exoproteases (peptidase) derived from animals (for example, pancreatin, trypsin, chymotrypsin, pepsin, and the like), derived from plants (for example, papain, bromelain, and the like), or derived from microorganisms (for example, lactobacillus, yeast, fungi, *Bacillus subtilis, Actinomyces*, and the like), roughly refined products thereof, cell debris, and the like.

The amount of the protease used with respect to the above-mentioned protein starting material varies depending on the concentration of the substrate, the titer of the enzyme, the reaction temperature, and the reaction time. However, in general, for each gram of protein starting material, hydrolysis can be carried out by the addition of enzyme at a ratio of 50 to 10,000 active units per 1 g of protein starting material either individually or in combination as a plurality. In addition, the addition of enzyme can be all at once, divided into small amounts, or into each type, or successively.

In addition, the pH for the protein hydrolysis reaction is selected from the range of pH 2 to 10 in accordance with the optimum pH for the enzyme being used. More specifically, this is carried out by adjusting the protein solution to the desired pH by the addition of acid or alkali within the range of pH 2 to 10 according to the type of enzyme being used, prior to the addition of the enzyme to the above-mentioned protein solution. In this case, examples of the acid are hydrochloric acid, citric acid, phosphoric acid, and the like, and examples of the alkali are sodium hydroxide, potassium hydroxide, potassium carbonate, and the like.

The temperature for the protein hydrolysis reaction is not particularly limited, and can be selected from a range which can be put into practical use and which includes the temperature range which is most suitable for the expression of the enzyme action, in other words, a range of normally 30 to 70° C. By means of maintaining the temperature above or below the optimum temperature for the enzyme, for example, in a range of 50 to 60° C., it is also possible to prevent spoiling during the protein hydrolysis reaction.

With regard to the time for the protein hydrolysis reaction, since the state of progress varies depending on the reaction conditions such as the type and combination of the enzymes used, the reaction temperature, and the initial pH, it is necessary to determine the duration time for the reaction at a range within which it is possible to adjust the rate of hydrolysis of the protein to 30 to 45% established by preliminary testing as explained above.

The termination of the enzyme reaction is carried out by the inactivation or removal of the enzymes when the degree of hydrolysis based on the hydrolysis conditions established by the preliminary testing is within the range that the rate of hydrolysis of protein is 30 to 45%. The inactivation operation can be carried out by means of heat treatment (for example, at 85° C. for 15 minutes, or the like). In addition, the removal operation can be carried out by means of ultrafiltration, or the like. After inactivation or removal of the enzyme in the hydrolysis solution, in accordance with need, precipitate is removed from the hydrolysis solution by means of an operation using diatomaceous earth (for example, cerite, or the like), microfiltration, ultrafiltration, centrifugal separation, and the like.

The solution containing the obtained protein hydrolysate can be used as it is, alternatively and in accordance with need, the solution can be concentrated using a known method such as a reverse osmosis membrane method, and used as a concentrated solution. Furthermore, this concentrated solution can be dried and powdered using a known method, which can then be dissolved in water at a predetermined concentration before being processed using a porous type synthetic adsorbent, which is carried out later.

The porous synthetic adsorbent used in the method of the present invention is a so-called porous type, and has a porous structure with a large number of fine pores having diameters of several nm to several tens of nm in its surface. The surface area of the resin is great and the adsorbence is high. These adsorbents are known to hydrophobically adsorb substances such as the odorous component, the bitter component, and amino acids based on Van der Vaal's forces, the renewal operations for removal of the adsorbed components are easy, and therefore they can be industrially used with ease.

In addition, the porous synthetic adsorbent is formed mainly from a copolymer of styrene and divinylbenzene, or methacrylic ester polymer as a matrix structure of resin. Since ion exchange groups have not been introduced into these resins, they are resistant with respect to chemical and physical treatment such as with heat, acids, and alkali. Therefore, their washing and sterilization is easy, and they are ideal for manufacturing food and drink products, and pharmaceutical products which require attention with regard to contamination by bacteria.

In addition, as the porous synthetic adsorbent, adsorbents having various different average pore size based on the type of resin are available commercially. Since the average pore size has a great influence on the affinity for the target material for adsorption, the size of the average pore radius is an indicator for selection of the adsorbent. Therefore, it is necessary to select the adsorbent based on the size of the average pore radius in accordance with the purpose.

As is clear from the Text Examples described below, in the method of the present invention, the use of two types of porous synthetic adsorbent having respectively an average pore radius of from 2 to 8 nm, and an average pore radius of from 20 to 30 nm is necessary for manufacturing with good efficiency a protein hydrolysate which has extremely low antigenicity and good emulsifiability.

As the porous synthetic adsorbent having an average pore radius of from 2 to 8 nm which is used in the method of the present invention, any porous synthetic adsorbent which has an average pore radius of from 2 to 8 nm is suitable, and examples include SEPABEADS SP-825, SEPABEADS SP-850, DIAION HP-21 (all manufactured by Mitsubishi Chemical Corporation), Amberlite XAD-4, Amberlite XAD-2000 (both made by Rohm and Haas Co.), and the like, which are commercially available.

As the porous synthetic adsorbent having an average pore radius of from 20 to 30 nm which is used in the method of the present invention, any porous synthetic adsorbent which has an average pore radius of from 20 to 30 nm is suitable, and examples include SEPABEADS HP-1MG, SEPABEADS SP-206, DIAION HP-20 (all manufactured by Mitsubishi Chemical Corporation), and the like, which are commercially available.

The adsorption treatment of the present invention carried out using this porous synthetic adsorbent is as follows. The adsorption treatment is carried out by adjusting the protein hydrolysate having a rate of hydrolysis of protein within the range of 30 to 45% to a solution having a concentration of 5 to 20%, and then bringing the solution into contact with the above-mentioned two types of porous hydrophobic synthetic adsorbent either simultaneously or individually.

It is preferable for the adsorption treatment to be carried out in a manner in which the contact between the above-mentioned protein hydrolysate and the above-mentioned two types of porous synthetic adsorbent occurs with good efficiency. More specifically, this can be carried out by either of a method in which a specified amount of porous synthetic adsorbent made into a slurry state is added to a container or tank holding a specified amount of protein hydrolysate solution, and then agitated slightly or left to stand for a predetermined period of time, or a method in which a specified amount of protein hydrolysate solution is passed through a column filed with a specified amount of the porous synthetic resin in such a manner that they make contact for a predetermined period of time.

When carrying out the adsorption treatment using the column method, the period of time for which the protein hydrolysate and the adsorbent are in contact is normally expressed by space velocity (space volume, hereinafter referred to as SV). The rate at which a given volume of protein hydrolysate solution passes through an equivalent amount of adsorbent in one hour is determined to be SV=1 (units; $h^{-1}$). The slower this rate, the longer the time that the protein hydrolysate solution and the synthetic adsorbent are in contact, and the greater the adsorbency. However, when it is extremely slow, production efficiency becomes poor, and therefore, normally, it is preferable for the column method to be conducted within a range of 0.5 to 5 $h^{-1}$, and more preferably, in a range of 1 to 3 $h^{-1}$.

In addition, with regard to the pH of the adsorption treatment since the mechanism of adsorption of the adsorption target material to the porous synthetic adsorbent is based in general on hydrophobic adsorption, it is preferable for this to be carried out in a pH range in which the adsorption target material does not have an electric charge, and usually, it is preferable for the adsorption treatment to be carried out in a pH range of 5 to 7.

In addition, as long as hygienic conditions, such as the bacterial growth, flavor and physical properties of the protein hydrolysate are considered, the temperature of the adsorption treatment is not particularly limited.

In addition, in the adsorption treatment, the above-mentioned two types of porous synthetic adsorbent can either be mixed and used together at the same time or they can be used separately. In more detail, the adsorption treatment can be carried out using one of either the porous synthetic adsorbent having an average pore radius of 2 to 8 nm, or the porous synthetic adsorbent having an average pore radius of 20 to 30 nm, and then the adsorption treatment is continued using the other of the porous synthetic adsorbents.

In addition, since the porous synthetic adsorbent has a porous structure, it has a large surface area, and it is necessary to adjust the amount (the contact surface area) of the porous synthetic adsorbent used in accordance with the amount of the adsorption target material. More specifically, if the amount of porous synthetic adsorbent used with respect to the adsorption target material is too great, in addition to the adsorption target material, the material desired for recovery will also be adsorbed, and the recovery efficiency will be degraded. On the other hand, if the amount of the porous synthetic adsorbent used with respect to the adsorption target material is too small, the removal of the adsorption target material is insufficient, and the reduction in antigenicity is insufficient.

In the method of the present invention, as is clear from the tests discussed below, it is necessary for the total surface area of the two types of porous synthetic adsorbent having respectively an average pore radius of 2 to 8 nm and 20 to 30 nm to be in the range of 300 to 3000 $m^2$ with respect to each 1 gram (protein equivalent) of protein hydrolysate having a rate of hydrolysis of protein adjusted as described above in a range of 30 to 45%, in order to manufacture at a high recovery rate a protein hydrolysate having low antigenicity and good emulsifiability.

The used adsorbent can be easily regenerated by removing the adsorption target materials such as adsorbed antigenic substances by washing with an acid or alkali agent, and therefore, it can be used repeatedly.

In addition, in the method of the present invention, the adsorbent can be used such that the ratio of the surface area of the porous synthetic adsorbent having an average pore radius of 2 to 8 nm to the surface area of the porous synthetic adsorbent having an average pore radius of 20 to 30 nm is in the range of 3:7 to 7:3. It is preferable for variation within this range in accordance with the rate of hydrolysis of the protein. When carrying out an adsorption treatment on a protein hydrolysate having a high rate of hydrolysis of the protein, it is preferable to increase the ratio of the surface area of the porous synthetic adsorbent having an average pore radius of 2 to 8 nm.

In addition, when the adsorbent used in the method of the present invention has a ratio of the surface area of the porous synthetic adsorbent having an average pore radius of 2 to 8 nm to the surface area of the porous synthetic adsorbent having an average pore radius of 20 to 30 nm of from 4:6 to 6:4, the recovery rate of the protein hydrolysate with respect to the protein starting material is even more superior, and therefore, this is preferable.

It is preferable for a filtration treatment such as ultrafiltration to be carried out on the obtained solution containing the protein hydrolysate. Specifically, this is done by carrying out a filtration treatment using a commercially available ultrafilter having a molecular weight cut off of 6000 Daltons or less, and in more detail, 1000 to 6000 Daltons, the high molecular weight material a part of which may remain is removed, and the fraction which passes through the filter is recovered.

The obtained solution containing the protein hydrolysate can be used as it is, or in accordance with need, this solution can be concentrated by means of a known method such as a reverse osmosis method and then used as a concentrated solution. Furthermore, this concentrated solution can be dried using a known method, and used as a powder.

By means of the above-mentioned method, it is possible for the antigenic material which remains in the protein hydrolysate to become effectively adhered to the porous hydrophobic synthetic adsorbent, and it is possible to excellently maintain the recovery rate of the protein hydrolysate with respect to the protein starting material. In addition, by means of the method of the present invention, it is possible to manufacture protein hydrolysate which is different to refined and isolated peptides, which is considered to have a much lower antigenicity when compared with all current conventional technologies, and which essentially does not have antigenicity.

By means of the above-mentioned method of the present invention, it is possible to manufacture the protein hydrolysate of the present invention, that is, a protein hydrolysate having the characteristics of a rate of hydrolysis of 30 to 45%, a number average molecular weight of 300 or less, and a ratio of the weight average molecular weight to the number average molecular weight of greater than 1 and 2 or less.

In the following, the protein hydrolysate of the present invention will be explained in detail. By having a rate of hydrolysis of 30 to 45% and a number average molecular weight of 300 or less, the protein hydrolysate of the present invention has reduced antigenicity and excellent emulsifiability. In addition, by having a ratio of the weight average molecular weight to the number average molecular weight of 2 or less, it is a protein hydrolysate which exhibits a molecular weight distribution which is approximated roughly to single distribution, from which impurities such as macromolecular antigenic substances have been adsorbed and removed, and which has excellent properties and substantially no antigenicity.

A ratio of the weight average molecular weight to the number average molecular weight of 1 only occurs when the protein hydrolysate is a substance which has a single molecular weight represented by a refined and isolated peptide. Consequently, it is easy to understand that by defining the ratio of the weight average molecular weight to the number average molecular weight of the protein hydrolysate as exceeding 1, the protein hydrolysate of the present invention is a composition containing at least two peptides having different molecular weights.

The protein hydrolysate of a first aspect of the present invention is considered to have excellent emulsifiability, and to have an antigenicity which is much lower compared with all current conventional technologies, and therefore has the superior characteristic of essentially not having antigenicity.

The food and drink products of the present invention contain the above-mentioned protein hydrolysate of the present invention.

Since the protein hydrolysate of the present invention has essentially no antigenicity, foods and drinks which contain it can be preferably used as foods and drinks for prevention of allergies or as foods and drinks for allergy patients.

In the present invention, food and drink products for the prevention of allergies indicates foods and drinks used, for the purpose of preventing allergies, as protein sources for infants, expectant and nursing mothers, and patients with reduced immune function, and these foods and drinks have had their antigenicity reduced sufficiently to be used for this purpose.

In addition, food and drink products for allergy patients indicates foods and drinks used as proteins sources which do not trigger allergic reactions in allergy patients, for whom it is clear that the ingestion of foods and drinks which have antigenicity trigger allergic reactions, and these indicated foods and drinks have had their antigenicity reduced sufficiently to be used for this purpose.

Furthermore, in addition to the protein hydrolysate of the present invention having essentially no antigenicity, it has excellent emulsifiability. Therefore, it can be preferably used as a starting material for modified milk and modified powdered milk. In more detail, the modified milk and modified powdered milk obtained from the protein hydrolysate of the present invention as a starting material does not have the problem of the separation out of fat of conventional antigenic modified milks, and is superior in appearance, flavor, and rates of absorption.

EXAMPLES

In the following, the present invention will be explained in detail giving Examples and Tests. However, the present invention is not limited to the following examples.

In the following Tests, the following test methods were used.

(1) Method for Calculation of the Rate of Hydrolysis of Protein

The total quantity of nitrogen in a sample is measured using the Kjeldahl method ("Food Analysis Methods", edited by the Japanese Food Industry Association, page 102, Kourin K K, 1984), the quantity of formol nitrogen in a sample is measured by means of a formol titration method (Mitsuda et al, "Food Engineering Experiments", First Volume, page 547, Yokendo, 1970), and from these measured values, the rate of hydrolysis is calculated using the following formula:

Rate of Hydrolysis (%)=(formal nitrogen quantity/total nitrogen quantity)×100

(2) Measurement Method for the Number Average Molecular Weight and the Weight Average Molecular Weight The number average molecular weight and the weight average molecular weight are measured using high performance liquid chromatography (Nobuo Ui et al, "High Performance Liquid Chromatography of Proteins/Peptides", Chemical Zoukan No. 102, page 241, Kagaku Doujin K K, 1984).

Specifically, a Poly Hydroxyethyl Aspartamide Column (manufactured by Poly LC, diameter of 4.6 mm and length of 400 mm) was used, and elution conducted at an elution speed of 0.5 ml/min using 20 mM of sodium chloride and 50 mM of formic acid. Detection was carried out using a UV detector (manufactured by Shimadzu Corporation, absorbance of 215 nm), the molecular weight distribution was measured, data analysis was carried out using a GPC analysis system (manufactured Shimadzu Corporation), and the number average molecular weight and the weight average molecular weight were calculated.

(3) Measurement Method for Remaining Antigenic Activity

This was measured using the sandwich ELISA method (Sunao Matsuhashi, et al, "Introduction to Immunology Experiments", page 160, Gakkai Shuppan Center, 1985).

More specifically, a rabbit is immunized with the antigenic protein, the specific IgG from the rabbit serum is purified and used. This is diluted with 0.1 M of bicarbonate buffer, 100 μl are pipetted into each well of a polystyrene microplate (made by Nunc Co.), and after being left to stand for 2 hours at 37° C., it is washed with PBS containing 0.05% Tween 20 (hereinafter referred to as PBS-Tween).

Next, 100 µl of PBS containing 1% gelatin (made by Bio-Rad Co.) is pipetted into each of the above-mentioned wells, and after being left to stand for 30 minutes at 37° C., it is washed with PBS-Tween. The sample and standard protein are respectively diluted with PBS-Tween and 100 µl is added to each of the above-mentioned wells, left to stand for 1 hour at 37° C., and then washed with PBS-Tween.

Biotinylated specific IgG is diluted with PBS-Tween, and 100 µl is pipetted into each of the above-mentioned wells, and after being left to stand for 1 hour at 37° C., it is washed with PBS Tween. Streptavidin and biotinylated peroxidase is dissolved in PBS, 100 µl is pipetted into each of the above-mentioned wells, and washed with PBS-Tween.

As the substrate, 100 µl of o-pherendiamine solution is pipetted into each of the above-mentioned wells, and allowed to react for 10 minutes in the dark at room temperature. Then 50 µl of 3M sulfuric acid is added to each well, and the reaction terminated.

Next, the absorbance at 492 nm of the reaction product is measured using a microplate reader, and the remaining antigenic activity of the sample is calculated by comparison with the measured value for the standard protein.

(4) Evaluation Method for Emulsifiability 100 g of the sample, 200 g of corn oil (manufactured by Taiyo-Yushi Co., Ltd.), and 4 g of lecithin (manufacture by Ajinomoto Co., Ltd.) are added to 300 ml of hot water (60° C.), and subjected to a preliminary emulsification using a TK homo-mixer (manufactured by Tokushu Kika Kogyo Co., Ltd.). The total amount is adjusted to 1000 ml by the addition of water, and then emulsified using a homogenizer (manufactured by APV Company) at a pressure of 5 MPa in the first stage, and 15 MPa in the second stage. The presence or absence of separation of the fat in the obtained emulsified product was observed with the naked eye, and the emulsifiability was evaluated according to the following evaluation standard.

Good: no fat separation

Bad: fat separation present (5) Calculation Method for the Recovery Rate of the Protein Hydrolysate The recovery rate (A) of protein hydrolysate is calculated using the following formula based on the dry weight of the protein starting material (B) and the dry weight of the obtained protein hydrolysate (C):

$$A(\%) = (C/B) \times 100$$

Example 1

1.3 kg of commercially available milk whey protein concentrate (having a protein equivalent of 1 kg, manufactured by Milei GmbH) was added to 9 kg of deionized water, and thereby 13 kg of whey protein solution having a protein concentration of approximately 10% was prepared. This whey protein solution was heat sterilized for 1 minute at 70° C. using a plate type heat exchanger, and then the temperature of the solution was adjusted to 53° C. The pH was adjusted to 9.5 using a 10% aqueous solution of sodium hydroxide and a 20% aqueous solution of potassium carbonate. For each 1 gram of protein, 500 active units of pancreatin F (manufactured by Amano Enzyme Inc.), 150 active units of protease N Amano (manufactured by Amano Enzyme Inc.), and 200 active units of Sumizyme LP20 (manufactured by Shin Nippon Kagaku Kogyo Company) were added in these proportions, and the protein hydrolysis reaction initiated. After 15 hours, when the rate of hydrolysis had become 35%, the enzymes were deactivated by raising the temperature to 120° C. for 15 seconds using a plate type heat exchanger, thereby terminating the enzyme reaction, and then the solution was cooled to 10° C.

This hydrolysis solution was filtered using an ultrafiltration membrane having a molecular weight cut-off of 20,000 (manufactured by Nitto Denko Corporation), the filtrate was freeze dried, and approximately 1090 g (a protein equivalent of 840 g) of powdered protein hydrolysate was obtained.

Next, the total amount of the obtained protein hydrolysate was dissolved in 9810 g of deionized water, and thereby 10.9 kg of an aqueous solution of protein hydrolysate having a concentration of approximately 10% was obtained.

Two types of porous synthetic adsorbent were used as the porous synthetic adsorbent. 720 g (having a surface area of 420,000 $m^2$) of a porous synthetic adsorbent having an average pore radius of 8 nm (DIAION HP-21, having a specific surface area of 583 $m^2/g$; manufactured by Mitsubishi Chemical Corporation) and 820 g (having a surface area of 420,000 $m^2$) of a porous synthetic adsorbent having an average pore radius of 26 nm (DIAION HP-20, having a specific surface area of 511 $m^2/g$, manufactured by Mitsubishi Chemical Corporation) were mixed at proportions to give a ratio of surface areas of 1:1 and a total amount of adsorbent of 1540 g, and this was charged into an acrylic column having a volume of 41.

The total amount of the above-mentioned protein hydrolysate aqueous solution was passed through the above-mentioned column charged with the porous synthetic adsorbents under the conditions of a flow rate of $SV=3h^{-1}$ and 10° C., and the protein hydrolysate brought into contact with the two types of adsorbent simultaneously. In other words, the contact was brought about under conditions in which the total surface area of the two types of porous synthetic adsorbent per 1 g (protein equivalent) of protein hydrolysate was 1000 $m^2$. The eluted liquid was recovered, and freeze dried, and thereby, approximately 910 g of protein hydrolysate (a protein equivalent of 700 g) was obtained.

The results of the tests on the obtained protein hydrolysate carried out using the above-mentioned test methods were an number average molecular weight of 260, a value for the ratio of the weight average molecular weight to the number average molecular weight of 1.8, a remaining antigenic activity of an extremely low $10^{-8}$, excellent emulsifiability, and a recovery rate of protein hydrolysate with respect to the protein starting material of 70%, which is excellent.

Example 2

120 g of commercially available milk casein (having a protein equivalent of 100 g, manufactured by New Zealand Dairy Board) was dispersed in 880 g of distilled water, the pH was adjusted to 7.0 using a 10% aqueous solution of sodium hydroxide to completely dissolve the casein, and thereby approximately 1 kg of an aqueous solution of casein having a protein concentration of approximately 10% was prepared. This aqueous solution of casein was heat sterilized for 15 minutes at 85° C., and then the temperature of the solution was adjusted to 50° C. The pH was adjusted to 8.5 using a 10% aqueous solution of potassium hydroxide. For each gram of protein, 400 active units of pancreatin F (manufactured by Amano Enzyme Inc.), 1250 active units of actinase AS (manufactured by Kaken Pharma Co.), and 250 active units of protease A Amano (manufactured by Amano Enzyme Inc.) were added in these proportions, and the protein hydrolysis reaction initiated. After 17 hours, when the rate of hydrolysis had become 38%, the enzymes were deactivated by raising the temperature to 90° C. for 20 minutes to terminate the enzyme reaction, and then the solution was cooled to 10° C.

Undissolved substances were removed from the hydrolysis solution by diatomaceous filtration, then the hydrolysis solution was freeze dried, and approximately 93 g (a protein equivalent of 78 g) of powdered protein hydrolysate was obtained.

Next, the total amount of the obtained protein hydrolysate was dissolved in 837 g of deionized water, and thereby 930 g of an aqueous solution of protein hydrolysate having a concentration of approximately 10% was obtained.

Two types of porous synthetic adsorbent were used as the porous synthetic adsorbent. 63 g (having a surface area of 62,400 m$^2$) of a porous synthetic adsorbent having an average pore radius of 4 nm (SEPABEADS SP-850, having a specific surface area of 995 m$^2$/g; manufactured by Mitsubishi Chemical Corporation) and 183 g (having a surface area of 93,600 m$^2$) of a porous synthetic adsorbent having an average pore radius of 26 nm (DIAION HP-20, having a specific surface area of 511 m$^2$/g, manufactured by Mitsubishi Chemical Corporation) were mixed at proportions to give a ratio of so-called surface areas of 4:6 and a total amount of adsorbent of 246 g, and this was packed into a glass column having a volume of 1000 ml.

The total amount of the above-mentioned aqueous solution of protein hydrolysate was passed through the above-mentioned column packed with the porous synthetic adsorbents under the conditions of a flow rate of SV=2h$^{-1}$ and 25° C., and the protein hydrolysate brought into contact with the two types of adsorbent simultaneously. In other words, the contact was brought about under conditions in which the total surface area of the two types of porous synthetic adsorbent per 1 g (protein equivalent) of protein hydrolysate was 2000 m$^2$. The eluted liquid was recovered, and freeze dried, and thereby, approximately 78 g of protein hydrolysate (a protein equivalent of 65 g) was obtained.

The results of the tests on the obtained protein hydrolysate carried out using the above-mentioned test methods were a number average molecular weight of 258, a value for the ratio of the weight average molecular weight to the number average molecular weight of 1.7, a remaining antigenic activity of an extremely low 10$^{-8}$, excellent emulsifiability, and a recovery rate of protein hydrolysate with respect to the protein starting material of 65%, which is excellent.

Comparative Example 1

A protein hydrolysate was manufactured following the method described in Example 1 of Japanese Examined Patent Application, Second Publication No. Sho 54-36235 (hereinafter referred to as Conventional Technique 1).

9 kg of water were added to 1 kg of commercially available casein (Hammerstein Casein, manufactured by Merck Co.), and fully dispersed. 2N aqueous solution of sodium hydroxide was added, the pH adjusted to 7.0, and the casein completely dissolved to make an approximately 10% aqueous solution of casein. This protein solution was sterilized for 15 minutes at 85° C., and then cooled to 50° C. With respect to each 1 g of protein, 1,000 active units of each of freeze dried disrupted cells of *Lactobacillus helveticus* (20,000 active units/g) (strain commercially available from Chr. Hansen Co.), official pancreatin (25,000 active units/g; manufactured by Amano Enzyme Inc.), and Amano A (80,000 active units/g; manufactured by Amano Enzyme Inc.) were added to this casein solution, with the total of the number of active units of the three types of enzyme being 3000 per 1 g of protein. Then, the temperature was maintained at 50° C. for 24 hours and the casein hydrolyzed. Thereafter, the enzymes were deactivated by raising the temperature to 80° C. for 15 minutes, the solution was cooled, and approximately 9.5 l of hydrolyzed casein solution was obtained.

Comparative Example 2

A protein hydrolysate was manufactured following the method described in Example 2 of Japanese Examined Patent Application, Second Publication No. Sho 62-61039 (hereinafter referred to as Conventional Technique 2).

Whey protein was subjected to continuous enzyme hydrolysis in an enzyme reactor using an ultrafiltration membrane having a cut off of 5000. The conditions were 40° C., pH 8.5, an initial protein content of 84.4g/l, 2HKOH as the base used, a ratio of the enzyme/substrate of 11.8%, the time of the preliminary hydrolysis was 2 hours, and the protein content of the solution supplied to the reactor was 45.5 g/l.

Comparative Example 3

A protein hydrolysate was manufactured following the method described in Example 1 of Japanese Examined Patent Application, Second Publication No. Sho 7-73507 (hereinafter referred to as Conventional Technique 3).

200 g of commercially available casein was dissolved in such a way as to be 10% by weight and the pH was adjusted to 8.0 using a 10% sodium hydroxide. After heat sterilization for 10 minutes at 90° C., the temperature was adjusted to 45° C. Then 10 g of pancreatin F (manufactured by Amano Enzyme Inc.), 2 g of protease N "Amano" (manufactured by Amano Enzyme Inc.), and 4 g of *Lactobacillus helveticus* cell extract (20,000 active units per 1 g) were added, and enzyme hydrolysis proceeded at 45° C. for 24 hours. After inactivation at 90° C. for 5 minutes, the precipitate was removed by filtration. The filtrate was freeze dried to give 170 g of a freeze dried product. 18 g of this freeze dried product was made into a 20% by weight aqueous solution, and after the removal of undissolved substances, it was eluted in a Sephadex G-10 column of 10×20 cm. Deionized water was used in the elution solution, and the rate was 10 ml/minute. The elution quantity of 200 to 500 ml was fractionated, freeze dried, and 6 g of dried product was obtained.

Comparative Example 4

A protein hydrolysate was manufactured following the method described in Example 1 of Japanese Patent No. 2959747 (hereinafter referred to as Conventional Technique 4).

1 kg of milk whey protein powder having a purity of 75% (manufactured by the California Protein Company) was dissolved in 9 kg of deionized water, sterilized by being maintained at 75° C. for 15 seconds, and the pH was adjusted to 9.0. Then, 1,800,000 PUN units (2400 PUN units per whey protein) of protease N Amano (manufactured by Amano Enzyme Inc.), and 68,000 active units of crushed cells of *Lactobacillus helveticus* (90 active units per 1 g of whey protein) were added, and hydrolysis conducted while being maintained at 50° C. The amount of free lysine was measured with the passage of time using a biotech analyzer (manufactured by Asahikasei Corporation), and when the amount of free lysine reached 14%, the enzymes were inactivated by heating at 80° C. for 6 minutes. After cooling, the pH was adjusted to 6.0 using citric acid. Then, ultrafiltration was carried out using an ultrafiltration membrane having a molecular weight cut off of 10,000 (Nitto Denko Co.), and approximately 16 kg of a solution containing 5.9% whey protein hydrolysate was obtained.

Comparative Example 5

A protein hydrolysate was manufactured following the method described in Example 1 of Japanese Unexamined Patent Application, First Publication, No. Hei 8-228692 (hereinafter referred to as Conventional Technique 5).

1 kg of commercially available casein (manufactured by New Zealand Dairy Board) was fully dispersed in 9 kg of water, a 10% aqueous solution of sodium hydroxide was added, and the pH was adjusted to 7.0 to completely dissolve the casein, and thereby an aqueous solution of casein having a concentration of approximately 10% was prepared. This aqueous solution of casein was heat sterilized for 10 minutes at 85° C., and then the temperature of the solution was adjusted to 50° C. The pH was adjusted to 9.5 by adding sodium hydroxide. Then, 1,008,000 active units (1,200 active units per 1 g of protein) of Bioplase SP-20 (manufactured by Nagase Biochemicals, Ltd.), 1,680,000 active units (2,000 active units per 1 g of protein) of protease N (manufactured by Amano Enzyme Inc.), and 5,880,000 active units (7,000 active units per 1 g of protein) of PTN 6.0S (manufactured by Novo Nordisk Co.) were added, and the hydrolysis reaction initiated. The rate of hydrolysis of the casein was measured over time, and the values for the total number of mols of 16 types of amino acids were measured using an L-amino acid sensor (Biotech Analyzer; manufactured by Asahikasei Corporation). When the rate of hydrolysis of the casein reached 24.1% and the measurement value according to the L-amino acid sensor reached 6.0 mM, the enzymes were deactivated by heating at 80° C. for 6 minutes, the enzyme reaction was terminated, and then it was cooled to 10° C. Standard Super Cell (manufactured by Tokyo Diatomaceous Earth Company) was added to this hydrolysis solution as a filter aid, and then suction filtration carried out. Next, the obtained filtrate was concentrated using a normal method, spray dried, and thereby 0.96 kg of a spray dried product was obtained.

Comparative Example 6

A protein hydrolysate was manufactured following the method described in Example 2 of Japanese Unexamined Patent Application, First Publication, No. Hei 7-203844 (hereinafter referred to as Conventional Technique 6).

3 kg of commercially available WPC (having a protein content of 85%; manufactured by Denmark Protein Company) were dissolved in 17 kg of purified water, and sterilized for 15 seconds at 75° C. in a plate sterilizer. Thereafter, the pH of the solution was adjusted to 8.0 by the addition of potassium hydroxide. Then, for each 1 g of protein, 1,000 PUN units of Bioplase (manufactured by Nagase Sangyo), 10,000 USP units of trypsin (manufactured by Novo Company), 2,000 PUN units of papain (manufactured by Amano Enzyme Inc.), and 200 PUN units of protease A Amano (manufactured by Amano Enzyme Inc.) were added in these proportions, and hydrolysis proceeded at 50° C. for 12 hours. Since the pH of the hydrolysis solution after the hydrolysis was 6.4, sodium hydroxide was added to adjust the pH to 7.3. Thereafter, the enzymes were deactivated by heating at 85° C. for 5 minutes and 130° C. for 2 seconds using a plate sterilizer. Then the hydrolysis solution was concentrated using a common method, dried and thereby 3 kg of powdered whey protein hydrolysate was obtained.

Test 1

This test was conducted to show that the protein hydrolysate and the manufacturing method therefor of the present invention are superior when compared with conventional techniques.

(1) Samples

The following seven types of samples were used.

The protein hydrolysate manufactured according to the method of Example 1 of the present invention The protein hydrolysate manufactured according to the method of Comparative Example 1 (the same method as Example 1 of Conventional Technique 1)

The protein hydrolysate manufactured according to the method of Comparative Example 2 (the same method as Example 2 of Conventional Technique 2)

The protein hydrolysate manufactured according to the method of Comparative Example 3 (the same method as Example 1 of Conventional Technique 3)

The protein hydrolysate manufactured according to the method of Comparative Example 4 (the same method as Example 1 of Conventional Technique 4)

The protein hydrolysate manufactured according to the method of Comparative Example 5 (the same method as Example 1 of Conventional Technique 5)

The protein hydrolysate manufactured according to the method of Comparative Example 6 (the same method as Example 2 of Conventional Technique 6)

(2) Test Method

The rate of hydrolysis, the number average molecular weight, the value of the ratio of the weight average molecular weight to the number average molecular weight (Mw/Mn), the remaining antigenic activity, and the emulsifiability of the protein of each sample were determined using the above-mentioned test methods.

(3) Test Results

The results of these tests are shown in Table 1. As is clear from Table 1, it has been ascertained that the protein hydrolysate of Example 1 of the present invention has extremely low antigenicity and is superior in emulsifiability when compared with the Comparative Examples 1 to 6 of the conventional techniques.

In addition, the samples of the present invention were suitably varied in the type of protein starting material, the rate of hydrolysis of the protein within the range of 30 to 45%, the number average molecular weight in a range of 300 or less, and a Mw/Mn in a range of greater than 1 and 2 or less, and tested, and approximately the same results were obtained.

TABLE 1

| Sample | Rate of Hydrolysis (%) | Mn | Mw/Mn | Remaining Antigenic Activity | Emulsifiability |
|---|---|---|---|---|---|
| Example 1 | 35 | 260 | 1.8 | $10^{-8}$ | good |
| Comparative Example 1 | 50.1 | 200 | 2.1 | $10^{-6}$ | bad |
| Comparative Example 2 | 35 | 270 | 2.3 | $10^{-6}$ | good |
| Comparative Example 3 | 43 | 230 | 2.2 | $10^{-6}$ | bad |
| Comparative Example 4 | 33 | 300 | 2.4 | $10^{-7}$ | good |
| Comparative Example 5 | 24.1 | 360 | 2.5 | $10^{-5}$ | good |
| Comparative Example 6 | 22 | 400 | 3.0 | $10^{-5}$ | good |

Test Example 2

This test was conducted to determine the appropriate rate of hydrolysis for the protein hydrolysate using remaining antigenic activity and emulsifiability as indicators.

(1) Preparation of Samples

Four types of samples (Examples 3 and 4, and Comparative Examples 7 and 8) were prepared using the same method as used in Example 1, except that the rate of hydrolysis of the protein starting material was stepwise changed as shown in Table 2, by varying the time of the termination of the enzyme reaction.

(2) Test Method

The rate of hydrolysis, the number average molecular weight, the value of the ratio of the weight average molecular weight to the number average molecular weight (Mw/Mn), the remaining antigenic activity, and the emulsifiability of the protein of each sample were determined using the above-mentioned test methods.

(3) Test Results

The results of these tests are shown in Table 2. As is clear from Table 2, it has been ascertained that in order to manufacture a protein hydrolysate which has extremely low antigenicity and which is superior in emulsifiability, it is necessary to change the rate of hydrolysis of the protein starting material to within a range of 30 to 45%.

In addition, it is shown that when the number average molecular weight is 300 or less, the remaining antigenic activity is extremely low, and in considering emulsifiability, a number average molecular weight of 200 or greater is preferable.

In addition, the tests were carried out by suitably varying the type of protein starting material, and the Mw/Mn within the range of greater than 1 and 2 or less, and approximately the same results were obtained.

TABLE 2

| Sample | Rate of Hydrolysis (%) | Mn | Mw/Mn | Remaining Antigenic Activity | Emulsifiability |
|---|---|---|---|---|---|
| Example 1 | 35 | 260 | 1.8 | $10^{-8}$ | good |
| Example 3 | 30 | 300 | 1.9 | $10^{-8}$ | good |
| Example 4 | 45 | 200 | 1.7 | $10^{-8}$ | good |
| Comparative Example 7 | 25 | 350 | 2.8 | $10^{-6}$ | good |
| Comparative Example 8 | 50 | 190 | 1.7 | $10^{-8}$ | bad |

Test Example 3

This test was performed to examine the size of the average pore radius of the porous hydrophobic synthetic adsorbent and combinations thereof using the remaining antigenic activity, the emulsifiability, and the recovery rate as indicators.

(1) Preparation of Samples

The twenty-eight samples (Examples 7 to 10, and Comparative Examples 9 to 32) shown below were prepared using the same method as for Example 1, except that the size of the average pore radius and the combinations thereof of the porous synthetic adsorbent were changed by using various types of commercially available porous synthetic adsorbents having different average pore radius sizes.

Example 7

A protein hydrolysate according to the present invention manufactured using the same method as used in Example 1 except that the two types of porous synthetic adsorbent used were a porous synthetic adsorbent having an average pore radius of 2 nm (trade name: SEPABEADS SP-825, manufactured by Mitsubishi Chemicals Corporation) and a porous synthetic adsorbent having an average pore radius of 20 nm (trade name: SEPABEADS HP-2MG, manufactured by Mitsubishi Chemicals Corporation).

Example 8

A protein hydrolysate according to the present invention manufactured using the same method as used in Example 1 except that the two types of porous synthetic adsorbent used were a porous synthetic adsorbent having an average pore radius of 2 nm and a porous synthetic adsorbent having an average pore radius of 30 nm (trade name: SEPABEADS SP-206, manufactured by Mitsubishi Chemicals Corporation).

Example 9

A protein hydrolysate according to the present invention manufactured using the same method as used in Example 1 except that the two types of porous synthetic adsorbent used were a porous synthetic adsorbent having an average pore radius of 8 nm and a porous synthetic adsorbent having an average pore radius of 20 nm.

Example 10

A protein hydrolysate according to the present invention manufactured using the same method as used in Example 1 except that the two types of porous synthetic adsorbent used were a porous synthetic adsorbent having an average pore radius of 8 nm and a porous synthetic adsorbent having an average pore radius of 30 nm.

Comparative Example 9

A protein hydrolysate manufactured using the same method as used in Example 1 except that a single porous synthetic adsorbent having an average pore radius of 1 nm (trade name: SEPABEADS SP-205, manufactured by Mitsubishi Chemicals Corporation) was used as the porous synthetic adsorbent.

Comparative Example 10

A protein hydrolysate manufactured using the same method as used in Example 1 except that a single porous synthetic adsorbent having an average pore radius of 2 nm was used as the porous synthetic adsorbent.

Comparative Example 11

A protein hydrolysate manufactured using the same method as used in Example 1 except that a single porous synthetic adsorbent having an average pore radius of 8 nm was used as the porous synthetic adsorbent.

Comparative Example 12

A protein hydrolysate manufactured using the same method as used in Example 1 except that a single porous synthetic adsorbent having an average pore radius of 10 nm (trade name: SEPABEADS SP-207, manufactured by Mitsubishi Chemicals Corporation) was used as the porous synthetic adsorbent.

Comparative Example 13

A protein hydrolysate manufactured using the same method as used in Example 1 except that a single porous synthetic adsorbent having an average pore radius of 20 nm was used as the porous synthetic adsorbent.

Comparative Example 14

A protein hydrolysate manufactured using the same method as used in Example 1 except that a single porous synthetic adsorbent having an average pore radius of 30 nm was used as the porous synthetic adsorbent.

Comparative Example 15

A protein hydrolysate manufactured using the same method as used in Example 1 except that a single porous synthetic adsorbent having an average pore radius of 40 nm (trade name: Amberlite X4D-9, manufactured by Rohm and Haas Co.) was used as the porous synthetic adsorbent.

Comparative Example 16

A protein hydrolysate manufactured using the same method as used in Example 1 except that that the two types of porous synthetic adsorbent used were a porous synthetic adsorbent having an average pore radius of 1 nm and a porous synthetic adsorbent having an average pore radius of 2 nm.

Comparative Example 17

A protein hydrolysate manufactured using the same method as used in Example 1 except that that the two types of porous synthetic adsorbent used were a porous synthetic adsorbent having an average pore radius of 1 nm and a porous synthetic adsorbent having an average pore radius of 8 nm.

Comparative Example 18

A protein hydrolysate manufactured using the same method as used in Example 1 except that that the two types of porous synthetic adsorbent used were a porous synthetic adsorbent having an average pore radius of 1 nm and a porous synthetic adsorbent having an average pore radius of 10 nm.

Comparative Example 19

A protein hydrolysate manufactured using the same method as used in Example 1 except that that the two types of porous synthetic adsorbent used were a porous synthetic adsorbent having an average pore radius of 1 nm and a porous synthetic adsorbent having an average pore radius of 20 nm.

Comparative Example 20

A protein hydrolysate manufactured using the same method as used in Example 1 except that that the two types of porous synthetic adsorbent used were a porous synthetic adsorbent having an average pore radius of 1 nm and a porous synthetic adsorbent having an average pore radius of 30 nm.

Comparative Example 21

A protein hydrolysate manufactured using the same method as used in Example 1 except that that the two types of porous synthetic adsorbent used were a porous synthetic adsorbent having an average pore radius of 1 nm and a porous synthetic adsorbent having an average pore radius of 40 nm.

Comparative Example 22

A protein hydrolysate manufactured using the same method as used in Example 1 except that that the two types of porous synthetic adsorbent used were a porous synthetic adsorbent having an average pore radius of 2 nm and a porous synthetic adsorbent having an average pore radius of 8 nm.

Comparative Example 23

A protein hydrolysate manufactured using the same method as used in Example 1 except that that the two types of porous synthetic adsorbent used were a porous synthetic adsorbent having an average pore radius of 2 nm and a porous synthetic adsorbent having an average pore radius of 10 nm.

Comparative Example 24

A protein hydrolysate manufactured using the same method as used in Example 1 except that that the two types of porous synthetic adsorbent used were a porous synthetic adsorbent having an average pore radius of 2 nm and a porous synthetic adsorbent having an average pore radius of 40 nm.

Comparative Example 25

A protein hydrolysate manufactured using the same method as used in Example 1 except that that the two types of porous synthetic adsorbent used were a porous synthetic adsorbent having an average pore radius of 8 nm and a porous synthetic adsorbent having an average pore radius of 10 nm.

Comparative Example 26

A protein hydrolysate manufactured using the same method as used in Example 1 except that that the two types of porous synthetic adsorbent used were a porous synthetic adsorbent having an average pore radius of 8 nm and a porous synthetic adsorbent having an average pore radius of 40 nm.

Comparative Example 27

A protein hydrolysate manufactured using the same method as used in Example 1 except that that the two types of porous synthetic adsorbent used were a porous synthetic adsorbent having an average pore radius of 10 nm and a porous synthetic adsorbent having an average pore radius of 20 nm.

Comparative Example 28

A protein hydrolysate manufactured using the same method as used in Example 1 except that that the two types of porous synthetic adsorbent used were a porous synthetic adsorbent having an average pore radius of 10 nm and a porous synthetic adsorbent having an average pore radius of 30 nm.

Comparative Example 29

A protein hydrolysate manufactured using the same method as used in Example 1 except that that the two types of porous synthetic adsorbent used were a porous synthetic adsorbent having an average pore radius of 10 nm and a porous synthetic adsorbent having an average pore radius of 40 nm.

Comparative Example 30

A protein hydrolysate manufactured using the same method as used in Example 1 except that that the two types of porous synthetic adsorbent used were a porous synthetic adsorbent having an average pore radius of 20 nm and a porous synthetic adsorbent having an average pore radius of 30 nm.

Comparative Example 31

A protein hydrolysate manufactured using the same method as used in Example 1 except that that the two types of porous synthetic adsorbent used were a porous synthetic adsorbent having an average pore radius of 20 nm and a porous synthetic adsorbent having an average pore radius of 40 nm.

Comparative Example 32

A protein hydrolysate manufactured using the same method as used in Example 1 except that that the two types of porous synthetic adsorbent used were a porous synthetic adsorbent having an average pore radius of 30 nm and a porous synthetic adsorbent having an average pore radius of 40 nm.

(2) Test Method

The remaining antigenic activity, the emulsifiability, and the recovery rate of the protein of each sample were determined using the above-mentioned test methods.

(3) Test Results

The results of these tests are shown in Table 3. As is clear from Table 3, it has been ascertained that in order to manufacture a protein hydrolysate which has extremely low antigenicity and which is superior in emulsifiability, at a high recovery rate of 60% or greater, it is necessary to use two porous synthetic adsorbents respectively having an average pore radius within the range of 2 to 8 nm, and an average pore radius within the range of 20 to 30 nm.

In addition, tests were conducted by suitably varying the type of protein starting material, the rate of hydrolysis of the protein within the range of 30 to 45%, and the total useable surface area of the above-mentioned two types of porous synthetic adsorbent within the range of 300 to 3000 m² for each 1 g (protein equivalent) of protein hydrolysate obtained by hydrolysis of the protein starting material to a rate of hydrolysis within the range of 30 to 45%, and approximately the same results were obtained.

TABLE 3

| Sample | Average pore radius of the porous synthetic adsorbent (nm) | Remaining antigenic activity | Emulsifi-ability | Recovery Rate (%) |
|---|---|---|---|---|
| Example 1 | 8 nm and 26 nm | $10^{-8}$ | good | 70 |
| Example 5 | 2 nm and 20 nm | $10^{-8}$ | good | 70 |
| Example 6 | 2 nm and 30 nm | $10^{-8}$ | good | 67 |
| Example 7 | 8 nm and 20 nm | $10^{-8}$ | good | 72 |
| Example 8 | 8 nm and 30 nm | $10^{-8}$ | good | 70 |
| Comparative Example 9 | 1 nm only | $10^{-5}$ | good | 88 |
| Comparative Example 10 | 2 nm only | $10^{-5}$ | good | 85 |
| Comparative Example 11 | 8 nm only | $10^{-5}$ | good | 81 |
| Comparative Example 12 | 10 nm only | $10^{-6}$ | good | 76 |
| Comparative Example 13 | 20 nm only | $10^{-7}$ | good | 70 |
| Comparative Example 14 | 30 nm only | $10^{-7}$ | good | 70 |
| Comparative Example 15 | 40 nm only | $10^{-8}$ | bad | 54 |
| Comparative Example 16 | 1 nm and 2 nm | $10^{-5}$ | good | 86 |
| Comparative Example 17 | 1 nm and 8 nm | $10^{-5}$ | good | 82 |
| Comparative Example 18 | 1 nm and 10 nm | $10^{-5}$ | good | 77 |
| Comparative Example 19 | 1 nm and 20 nm | $10^{-6}$ | good | 72 |
| Comparative Example 20 | 1 nm and 30 nm | $10^{-7}$ | good | 68 |
| Comparative Example 21 | 1 nm and 40 nm | $10^{-7}$ | bad | 62 |
| Comparative Example 22 | 2 nm and 8 nm | $10^{-5}$ | good | 79 |
| Comparative Example 23 | 2 nm and 10 nm | $10^{-6}$ | good | 75 |
| Comparative Example 24 | 2 nm and 40 nm | $10^{-8}$ | bad | 59 |
| Comparative Example 25 | 8 nm and 10 nm | $10^{-6}$ | good | 76 |
| Comparative Example 26 | 8 nm and 40 nm | $10^{-8}$ | bad | 58 |
| Comparative Example 27 | 10 nm and 20 nm | $10^{-8}$ | bad | 62 |
| Comparative Example 28 | 10 nm and 30 nm | $10^{-8}$ | bad | 61 |
| Comparative Example 29 | 10 nm and 40 nm | $10^{-8}$ | bad | 55 |
| Comparative Example 30 | 20 nm and 30 nm | $10^{-8}$ | bad | 51 |
| Comparative Example 31 | 20 nm and 40 nm | $10^{-8}$ | bad | 45 |
| Comparative Example 32 | 30 nm and 40 nm | $10^{-8}$ | bad | 41 |

Test Example 4

This test was conducted in order to examine the usable surface area of the porous synthetic adsorbent and the appropriate ratio for the weight average molecular weight to the number average molecular weight of the protein hydrolysate, using antigenicity and the recovery rate as indicators.

(1) Preparation of Samples

As shown in Table 4, four types of samples (Examples 9 and 10, and Comparative Examples 33 and 34) were prepared using the same method as used in Example 1, except for changes in the used surface area (m²) of the porous synthetic adsorbent with respect to each 1 g (protein equivalent) of protein hydrolysate.

(2) Test Method

The value of the ratio of the weight average molecular weight to the number average molecular weight (Mw/Mn), the remaining antigenic activity, and the recovery rate for each sample were determined using the above-mentioned test methods.

(3) Test Results

The results of these tests are shown in Table 4. As is clear from Table 4, it has been ascertained that in the manufacture of a protein hydrolysate which has extremely low antigenicity and which has a superior recovery rate, it is necessary for the total surface area of the two porous synthetic adsorbents (respectively having an average pore radius within the range of 2 to 8 nm, and an average pore radius within the range of 20 to 30 nm) used to be within the range of 300 to 3000 m² with respect to each 1 g (protein equivalent) of protein hydrolysate obtained by hydrolysis of the protein starting material to a rate of hydrolysis within a range of 30 to 45%. In addition, it was ascertained that when the ratio of the weight average molecular weight to the number average molecular weight of the protein hydrolysate is 2 or less, the antigenicity is extremely low.

In addition, tests were carried out by appropriately varying the type of protein starting material, the rate of hydrolysis of the protein within the range of 30 to 45%, and the number average molecular weight to 300 or less, and by appropriately varying the size and combination of the average pore radiuss of the porous synthetic adsorbents used to a combination of two types of porous hydrophobic synthetic adsorbent respectively having an average pore radius of 2 to 8 nm and an average pore radius of 20 to 30 nm, and approximately the same results were obtained.

TABLE 4

| Sample | Usable surface area of the porous synthetic adsorbent (m²) | Mw/Mn | Remaining antigenic activity | Recovery Rate (%) |
| --- | --- | --- | --- | --- |
| Example 1 | 1000 | 1.8 | $10^{-8}$ | 70 |
| Example 9 | 300 | 2.0 | $10^{-8}$ | 75 |
| Example 10 | 3000 | 1.7 | $10^{-8}$ | 65 |
| Comparative Example 33 | 200 | 2.1 | $10^{-7}$ | 85 |
| Comparative Example 34 | 4000 | 1.5 | $10^{-8}$ | 53 |

Test 5

This test was performed to investigate the preferable range for the ratio of the surface area of the porous synthetic adsorbent having an average pore radius of 2 to 8 nm to the surface area of the porous synthetic adsorbent having an average pore radius of 20 to 30 nm, using the remaining antigenic activity and the recovery rate as indicators.

(1) Preparation of Samples

As shown in Table 5, four samples (Examples 11 and 12, and Comparative Examples 35 and 36) were prepared using the same method as used in Example 1, with the exception of changes to the ratio of the surface area of the porous synthetic adsorbent having an average pore radius of 8 nm to the porous synthetic adsorbent having an average pore radius of 26 nm.

(2) Test Methods

The remaining antigenic activity and the recovery rate of each sample were determined according to the test methods discussed above.

(3) Test Results

The test results are shown in Table 5. As is clear from Table 5, in order to manufacture a protein hydrolysate having extremely low antigenicity at an even higher recovery rate, it is preferable for the ratio of the porous synthetic adsorbent having an average pore radius of 2 to 8 nm to the porous synthetic adsorbent having an average pore radius of 20 to 30 nm to be a surface ratio in the range of 4:6 to 6:4.

In addition, tests were carried out by appropriately varying the type of protein starting material, the rate of hydrolysis of the protein within the range of 30 to 45%, the size and combination of the average pore radiuss of the porous synthetic adsorbents used to a combination of two types of porous synthetic adsorbent respectively having an average pore radius of 2 to 8 nm and an average pore radius of 20 to 30 nm, and the total useable surface area of the two types of porous synthetic adsorbent to within a range of 300 to 3000 m² with respect to each 1 g (protein equivalent) of protein hydrolysate obtained by hydrolysis of the protein starting material to a rate of hydrolysis within a range of 30 to 45%, and approximately the same results were obtained.

TABLE 5

| Sample | Ratio of surface area of the two synthetic adsorbents (average pore radius 8 nm:average pore radius 26 nm) | Remaining antigenic activity | Recovery Rate (%) |
| --- | --- | --- | --- |
| Example 1 | 1:1 | $10^{-8}$ | 70 |
| Example 11 | 4:6 | $10^{-8}$ | 70 |
| Example 12 | 6:5 | $10^{-8}$ | 74 |
| Comparative Example 35 | 3:7 | $10^{-8}$ | 65 |
| Comparative Example 36 | 7:3 | $10^{-8}$ | 69 |

Example 13

25 kg of protein hydrolysate manufactured according to the method of Example 1, 68 kg of lactose (manufactured by Meggle Company), 1120 g of raffinose (manufactured by Nippon Beet Sugar Manufacturing Co., Ltd.), 14.6 kg of maltodextrine (manufactured by Matsutani Chemical Industry Co., Ltd.), 920 g of a mineral mixture (manufactured by Tomita Pharmaceutical Co., Ltd.), and 35 g of a vitamin mixture (manufactured by Tanabe Seiyaku Co., Ltd.) were dissolved in 300 kg of purified water. To this, 450 g of monoglyceride succinate (manufactured by Kao Corporation) and 40 kg of modified fat (manufactured by Taiyo-Yushi Co., Ltd.) were added, homogenized, sterilized at 120° C. for 2 seconds, concentrated, spray dried, and thereby 145 kg of powdered milk for the prevention of allergies was obtained.

Formulated milk containing the obtained powdered milk for the prevention of allergies at a concentration of 14% has good emulsifiability and flavor, and the remaining antigenic activity of the protein component is extremely low, therefore, it is ideal as a drink for the prevention of allergies.

Example 14

16 kg of protein hydrolysate manufactured according to the same method as Example 2, 500 g of lactulose (manufactured by Morinaga Milk Industry Co., Ltd.), 500 g of raffinose (manufactured by Nippon Beet Sugar Manufacturing Co., Ltd.), 62 kg of maltodextrine (manufactured by Matsutani Chemical Industry Co., Ltd.), 3 kg of tapioca powder (manufactured by Matsutani Chemical Industry Co., Ltd.), 920 g of a mineral mixture (manufactured by Tomita Pharmaceutical Co., Ltd.), and 35 g of a vitamin mixture (manufactured by Tanabe Seiyaku Co., Ltd.) were dissolved in 620 kg of purified water. To this, 20 kg of modified fat (manufactured by Taiyo-Yushi Co., Ltd.) were added, homogenized, and sterilized at 80° C. for 6 minutes, and thereby approximately 600 kg of modified milk for allergy patients were obtained.

The obtained modified milk for allergy patients had good emulsifiability and flavor, and the remaining antigenic activity of the protein component was extremely low. Therefore, it is ideal as a drink for allergy patients.

Example 15

5 kg of protein hydrolysate manufactured according to the same method as Example 1, and 15 kg of dextrine (manufactured by Sanmatsu Kogyo Co., Ltd.) were added to 7 kg of hot water (60° C.), and dissolved and dispersed using a TK homomixer (manufactured by Tokushu Kika Co., Ltd.), and thereby a liquid product was prepared.

To this liquid product, 140 g of monoglyceride succinate (manufactured by Kao Corporation), 2.2 kg of modified fat (manufactured by Taiyo-Yushi Co., Ltd.), 400 g of a mineral mixture (manufactured by Tomita Pharmaceutical Co., Ltd.), and 20 g of a vitamin mixture (manufactured by Tanabe Seiyaku Co., Ltd.) were added and subjected to a preliminary emulsification using a TK homomixer (manufactured by Tokushu Kika Co., Ltd.), and then water was added to bring the total amount to 100 kg.

Next, the preliminarily emulsified product was homogenized by being subjected to five repetitions of a two-stage treatment of a 5 MPa first stage and a 50 MPa second stage using a high pressure homomixer (manufactured by Manton Gaulin Co.), and thereby 92 kg of a liquid food were prepared.

Approximately 11 kg of this liquid food was filled into retortable pouches (manufactured by Toyo-Seikan Kaisha Ltd.) in 200 ml amounts. Thereafter, they were sterilized at 125° C. for 10 minutes using a retort sterilizer (manufactured by Hisaka Works, Ltd), and thereby 50 units of liquid food for allergy patients was prepared.

The obtained liquid food for allergy treatment had good emulsifiability and flavor, and the remaining antigenic activity of the protein component was extremely low. Therefore, it is suitable as a food or drink for allergy patients.

INDUSTRIAL APPLICABILITY

By the manufacturing method of the protein hydrolysate of the present invention, it is possible to manufacture a protein hydrolysate which has low antigenicity and superior emulsifiability, while maintaining an excellent recovery rate of protein hydrolysate with respect to the protein starting material, and this protein hydrolysate can be used by people who have a predisposition to incidence of allergy.

The protein hydrolysate of the present invention has excellent emulsifiability and essentially has no antigenicity, and therefore it can be used as a food or drink for the prevention of incidence of allergy and for allergy patients.

Foods and drinks which contain the protein hydrolysate of the present invention have good emulsifiability and flavor, the remaining antigenic activity of the protein component is extremely low. Therefore, they are useful as foods for the prevention of incidence of allergy diseases and as protein sources for allergy patients, such as low antigenic modified milk and modified powdered milk. Specifically, various types of foods and drinks such as modified powdered milk, modified milk, nutritional supplements, nutritional foods for the sick, and liquid foods, can be given as examples.

What is claimed is:

1. A method of manufacturing protein hydrolysate at a recovery rate of 60% or higher, the method comprising the steps of:
    carrying out hydrolysis of a protein starting material to a rate of hydrolysis within a range of 30 to 45%; and
    bringing an obtained protein hydrolysate into contact simultaneously or separately with two types of porous synthetic adsorbent respectively having an average pore radius in a range of 2 to 8 nm and an average pore radius in a range of 20 to 30 nm, the total surface area of the two porous synthetic adsorbents being in a range of 300 to 3000 $m^2$ per 1 g of the obtained protein hydrolysate, and
    recovering a non-adsorbed component.

2. A method of manufacturing protein hydrolysate according to claim 1, wherein the porous synthetic adsorbent having an average pore radius in a range of 2 to 8 nm and the porous synthetic adsorbent having an average pore radius in a ran ne of 20 to 30 nm are used such that a ratio of a surface area of the porous synthic adsorbent having an average pore radius in a range of 2 to 8 nm to a surface area of the porous synthetic adsorbent having an average pore radius in a ranae of 20 to 30 nm is in a range of 4:6 to 6:4.

* * * * *